United States Patent [19]

Horwath et al.

[11] B 4,001,083

[45] Jan. 4, 1977

[54] PROCESS FOR PRODUCING ISOAMYLASE

[75] Inventors: Robert Otto Horwath, Westport; Philip Rotheim, Stamford, both of Conn.

[73] Assignee: Standard Brands Incorporated, New York, N.Y.

[22] Filed: Apr. 8, 1975

[21] Appl. No.: 566,585

[44] Published under the second Trial Voluntary Protest Program on March 2, 1976 as document No. B 566,585.

Related U.S. Application Data

[63] Continuation-in-part of Ser. No. 395,501, Sept. 10, 1973, abandoned.

[52] U.S. Cl. .................................. 195/65; 195/114
[51] Int. Cl.² ........................................ C12D 13/10
[58] Field of Search ................... 195/65, 66 R, 114

[56] References Cited

UNITED STATES PATENTS

| | | | |
|---|---|---|---|
| 3,622,460 | 5/1968 | Masuda et al. ................. | 195/66 R |
| 3,790,446 | 2/1974 | Smith ............................. | 195/66 R |
| 3,806,419 | 4/1974 | Heady ............................ | 195/66 R |

*Primary Examiner*—Lionel M. Shapiro

[57] ABSTRACT

Microorganisms which produce isoamylase are propagated under aerobic conditions in an aqueous nutrient medium having present maltitol. The presence of the maltitol induces the microorganisms to produce greater amounts of isoamylase as compared to the amounts of isoamylase produced by propagating the microorganisms without the presence of maltitol.

10 Claims, No Drawings

PROCESS FOR PRODUCING ISOAMYLASE

This application is a continuation-in-part of application Ser. No. 395,501 filed on Sept. 10, 1973, now abandoned.

This invention relates to a process for producing isoamylase. More particularly, this invention relates to a process for propagating microorganisms which produce isoamylase under aerobic conditions in an aqueous nutrient medium having present maltitol.

Enzymes which effect the hydrolytic cleavage of starch are referred to in the art as amylolytic enzymes or amylases and may be derived from fungal and bacterial sources and from malt.

A number of different amylases have been identified on the basis of their particular hydrolytic effects on the amylose and amylopectin components of starch. Alpha-amylase hydrolyses the $\alpha$-1, 4 linkages in both amylose and amylopectin and in commercial practice is generally used to liquefy starch to reduce its viscosity. Beta-amylase has a saccharifying effect on starch resulting from its ability to hydrolyze the $\alpha$-1, 4 linkages at the ends of the amylose and amylopectin chains and thus split off maltose units from the chain ends. Another amylolytic enzyme, glucoamylase, hydrolyses starch to glucose. None of the aforementioned amylases, with the exception of glucoamylase, can act upon the $\alpha$-1, 6 glucosidic interchain linkages in amylopectin, glycogen or their degradation products.

Amylolytic enzymes which hydrolyse the $\alpha$-1, 6 glucosidic interchain linkages in amylopectin are broadly referred to in the art as $\alpha$-1, 6 glucosidases. A number of enzymes having considerably different specificities have been identified in the art as being capable of hydrolysing $\alpha$-1, 6 glucosidic interchain linkages. Of these, the two most important enzymes from the commercial standpoint are pullulanase and isoamylase. The major difference in regard to the specificity of these enzymes is that pullulanase will degrade the linear polysaccharide pullulan whereas isoamylase will not to a significant degree.

There are a number of patents which disclose methods of producing isoamylase and pullulanase. Canadian Pat. No. 852,196 to Ueda et al. describes a process for producing isoamylase by cultivating a strain of Escherichia intermedia in a fermentation medium comprising dextrin, peptone and inorganic salts. U.S. Pat. No. 3,490,995 to Wallenfels et al. discloses a process for producing cell-bound pullulanase from Aerobacter aerogenes in a culture medium wherein the carbon sources comprise maltose and pullulan or glycerin. U.S. Pat. No. 3,560,345 to Yokobayashi et al. describes a process for producing isoamylase by propagating *Pseudomonas amyloderamosa* in a culture medium containing as carbon sources starch, starch derivatives or maltose. U.S. Pat. No. 3,622,460 to Masuda et al. discloses a process for producing isoamylase by culturing a strain of Aerobacter aerogenes in a medium containing an ammonium salt and liquified starch. U.S. Pat. No. 3,790,446 and corresponding German Pat. No. 2,162,923 and Netherlands Pat. No. 7,117,405 to Gunja-Smith disclose the production of isoamylase by Cytophaga NCIB 9497. According to Mitchell et al. (J. Appl. Bacteriol., Vol. 32, pp. 40–50, 1969) and Manners et al. (Biochem J., Vol. 135, pp. 11–18, 1973), however, the microorganism designated Cytophaga NCIB 9497 may be a Flavobacterium and not a member of the Cytophaga genus. U.S. Pat. No. 3,806,419 to Heady discloses a method of preparing pullulanase by propagating *Aerobacter aerogenes* in a medium providing as a carbohydrate source a starch or a low D.E. starch hydrolysate.

One of the most important considerations in regard to commercial production of enzymes, and specifically of isoamylase, is the yield thereof. The yields of enzymes must be such that their use is economical.

Accordingly, it is the principal object of the present invention to provide a process for producing isoamylase in high yields.

This object and other objects of the present invention, which will be apparent from the following description, may be attained in accordance with the present invention by propagating microorganisms which produce isoamylase under suitable aerobic conditions in an aqueous nutrient medium having present an amount of maltitol sufficient to increase the amount of isoamylase produced over the amount of isoamylase produced by propagating the microorganisms without the presence of maltitol.

It is a preferred embodiment that the microorganisms which produce isoamylase used in the process of the present invention be selected from the genera Arthrobacter, Flavobacterium and Micrococcus. Particularly preferred species of microorganisms from the aforementioned genera are Flavobacterium sp. ATCC 21918, Micrococcus sp. ATCC 21919 and Arthrobacter sp. ATCC 21920.

Except where otherwise indicated, the bacteriological characteristics of the above identified species were determined according to the methods described in Society of American Bacteriologists' Manual of Microbiological Methods, McGraw-Hill Book Co., New York, N. Y. (1957) and are set forth below.

Bacteriological Characteristics of
Flavobacterium sp. ATCC 21918

| | |
|---|---|
| Gram reaction: | gram-negative |
| Morphology: | tapered rods, usually in pairs |
| Motility:[1] | motile, peritrichous flagella observed |
| Catalase: | positive |
| Oxidase: | negative |
| Desoxycholate agar: | no growth |
| Pigment: | No pigment produced on nutrient agar medium and on Pseudomonas P medium; soluble brown-black pigment produced in Azotomonas medium[2] |
| Fluorescent pigment: | none |
| Cellulose: | negative |
| Indole: | no growth |
| Methyl Red: | negative |
| Voges Proskauer: | negative |
| Pectate: | negative |
| Mucate: | negative |
| Lipase: | negative |
| Acetate: | positive |
| Aesculin: | no growth, inhibition |
| Egg yolk: | no growth |
| Simmons citrate: | positive |
| Kosers citrate: | positive |
| Decarboxylase: | |
| Lysine: | no growth |
| Ornithine: | no growth |
| Arginine: | no growth |
| $H_2S$ Production: | negative |
| Urea: | degradation, alkaline reaction |
| KCN: | negative |
| Phenylalanine: | no growth |
| Malonate: | no growth |
| Litmus milk: | slight alkaline |
| Casein hydrolysis: | negative |
| Growth in artificial sea water medium: | no growth |

-continued
Bacteriological Characteristics of Flavobacterium sp. ATCC 21918

| | |
|---|---|
| Growth in the presence of NaCl: | |
| 5% NaCl: | no growth |
| 7% NaCl: | no growth |
| 10% NaCl: | no growth |
| Temperature: | |
| 10°C: | no growth |
| 30°C: | growth |
| 37°C: | growth |
| 40°C: | no growth |
| 45°C: | no growth |
| Oxidation-Fermentation of Carbohydrates:[3] | |
| Adonitol: | growth, no pH change |
| Arabinose: | growth, no pH change |
| Dextrose: | growth, pH increased |
| Dextrose closed: | no growth |
| Cellobiose: | growth, no pH change |
| Fructose: | growth, pH increased |
| Glycerol | growth, no pH change |
| Mannitol: | growth, pH increased |
| Sucrose: | growth, pH increased |
| Trehalose: | growth, pH increased |
| Xylose: | growth, no pH change |
| Maltose: | growth, no pH change |
| Lactose: | growth, pH increased |
| Galactose: | growth, pH increased |
| Growth Response in Peptone-free, Purple Broth Carbohydrate medium:[4] | |
| Glucose: | growth, acid produced |
| Xylose: | growth, acid produced |
| Arabinose: | growth, acid produced |
| Sucrose: | growth, acid produced |
| Lactose: | weak growth, only slight acid produced |
| Mannitol: | growth, no acid produced, no fermentation |

[1]Flagella stain: E. Leifson, Atlas of Bacterial Flagellation, Academic Press (1960).
[2]Azotomonas medium: ATCC Catalog of Strains, Medium 16, p. 267 (1974).
[3]O-F Carbohydrates: R. Hugh & E. Leifson, J. Bacteriol., 66, pp. 24–26 (1953).
[4]Peptone-free Purple Broth: Ruth Gordon, Genus Bacillus Manual, USDA Handbook, No. 427 (1974).

Bacteriological Characteristics of Arthrobacter sp. ATCC 21920

| | |
|---|---|
| Gram stain: | gram-positive rods |
| Motility: | positive |
| Catalase: | positive |
| Oxidase: | negative |
| Desoxycholate: | no growth |
| Pigment: | light brown (soluble) |
| Fluorescent pigment: | none at 7 days; slight pigment at 14 days |
| Hexadecane as sole source of carbon: | growth white, no pigment |
| Acid fast stain | negative |
| Indole: | negative |
| Methyl Red: | negative |
| Voges Proskauer: | negative |
| Simmons citrate: | negative |
| Kosers citrate: | positive |
| Urea: | negative |
| Litmus milk: | alkaline |
| Casein hydrolysis: | positive |
| Gelatin: | positive |
| H$_2$S Production: | negative |
| Tellurite: | no growth |
| Growth anaerobically: | no growth |
| Nitrate Reduction: | positive (no gas) |
| Gordon's nitrate to nitrate: | positive (no gas) |
| Growth in NaCl: | |
| 5% NaCl: | no growth |
| 7% NaCl: | no growth |
| 10% NaCl: | no growth |
| Temperature: | |
| 10°C: | growth |
| 26°C: | growth |
| 30°C: | growth |
| 37°C: | growth |
| 45°C: | no growth |
| 50°C: | no growth |

-continued
Bacteriological Characteristics of Arthrobacter sp. ATCC 21920

| | |
|---|---|
| Methylene blue reduction: | positive, slow |

The bacteriological characteristics of Micrococcus sp. ATCC 21919 were determined according to the methods described in the above identified Society of American Bacteriologists' Manual of Microbiological Methods and A Guide to the Identification of the Genera of Bacteria, 2nd Ed., The Williams & Wilkins Company, Baltimore, Md. (1967).

Bacteriological Characteristics of Micrococcus sp. ATCC 21919

| | |
|---|---|
| Morphology: | spherical |
| Size: | 0.7 to 1.0 microns in diameter, arranged singly, in pairs, and in irregular clusters. |
| Spore: | none |
| Flagellum: | none |
| Motility: | none |
| Gram stain: | gram-positive |
| Catalase: | weakly positive |
| Oxidase: | negative |
| Oxidation-Fermentation Media: | Produces slight acid in aerobic sugar tubes but no acid from anaerobic tubes. |
| Cellulolytic Activity: | negative |
| Litmus Milk: | Slightly acid, no coagulation |
| Gelatin: | negative |
| Starch Agar (Difco): | no hydrolysis |
| Pigment: | Bright yellow, glistening raised colonies on Nutrient Agar and Brainhart Infusion Agar. |
| Potato Dextrose Agar: | no growth |
| Nitrate Reduction: | negative |
| Ornithine Decarboxylase: | negative |
| Indole: | negative |
| Fermentation of: | |
| Glucose: | positive |
| Lactose: | positive |
| Sucrose: | positive |
| Urease: | negative |
| Citrate Utilization: | negative |
| Lysine Decarboxylase: | negative |

The amount of maltitol present during the propagation of isoamylase-producing microorganisms may vary over a relatively wide range and is dependent upon many factors, such as the species of isoamylase-producing microorganisms being propagated, the temperature and pH at which the propagation is performed and the composition of the propagation medium. The minimum amount of maltitol which should be present is sufficient to induce the microorganisms to produce measurably greater amounts of isoamylase as compared to the amount of isoamylase produced by propagating the microorganisms without the presence of maltitol. The optimum amount of maltitol present is that amount which results in the greatest increase in isoamylase production. At higher levels of maltitol no further increase in isoamylase production is observed and, therefore, such levels are not recommended for reasons of economics. Generally, satisfactory results are achieved at maltitol levels of from about 0.2 to about 1.0 percent by weight based upon the volume of the propagation medium. The preferred amount of maltitol present in the propagation medium is from about 0.3 to about 0.8 percent based upon the same weight-volume basis.

A variety of carbon sources may be used in the propagation medium such as maltose, glucose, and the like.

Also, a variety of nitrogen sources such as sodium glutamate, ammonium salts and other substances which are commonly used in the propagation of microorganisms may be used.

The pH and the temperature of the propagation medium may also vary but, of course, should not be such that would result in inactivating or otherwise detrimentally affecting the microorganisms to such an extent that the production of isoamylase is significantly decreased. Generally, a pH in the range of from about 6 to about 7 and a temperature of from about 20° to about 30°C. provides satisfactory results.

In order to more clearly describe the nature of the present invention, specific examples will hereafter be described. It should be understood, however, that this is done solely by way of example and is intended neither to delineate the scope of the invention nor limit the ambit of the appended claims. In the examples and throughout the specification, percentages are utilized to refer to percent on a weight/volume basis unless otherwise specified.

The analytical procedure used for determining isoamylase in the following examples was performed using an automated procedure adapted from the method disclosed by Yokobayashi et al. in Biochimica et Biophysica Acta, Vol. 212, p. 459 (1970). The procedure was modified by replacing the 1.0 percent soluble glutinous rice starch with 0.25 percent amylopectin, replacing the 0.01 M iodine-potassium iodide solution with a 0.0025 normal iodine-potassium iodide solution, and performing the procedure at a pH of 5 and a temperature of 45°C. The amylopectin substrate was prepared from waxy maize starch purified by the method described by Schoch in Methods of Enzymology, Vol. III, p. 10 (1957).

The analytical procedure is based upon the ability of debranching enzymes acting on amylopectin to form amylose. Amylose, produced by such debranching activity in a fixed time and under suitable conditions, is reacted with an iodine-potassium iodide solution to form a soluble amylose-iodine complex. The intensity of the color of the blue amylose-iodine complex is measured in a colorimeter at 610 nm and recorded on a strip-chart recorder as a peak, the magnitude of which is proportional to the debranching activity of the enzyme. Debranching enzyme activity is expressed in terms of International Units per ml of sample (IU/ml) by comparing the magnitude of the peaks obtained with those obtained with a series of pullulanase enzyme standards, ranging from 0.3 to 3.0 IU/ml, by the aforedescribed automated procedure.

EXAMPLE I

This example illustrates propagating microorganisms which produce isoamylase in a medium containing maltitol and compares the yield of isoamylase obtained with the yield of isoamylase obtained by propagating the microorganisms without the presence of maltitol.

Flavobacterium sp. ATCC 21918, Micrococcus sp. ATCC 21919 and Arthrobacter sp. ATCC 21920 were propagated in the following culture media:

| Comp. of Medium A* | | Comp. of Medium B* | |
|---|---|---|---|
| Ingredient | %W/V | Ingredient | %W/V |
| Maltitol | 0.7 | Maltose | 2.0 |
| Maltose | 0.2 | Monosodium glutamate | 0.3 |
| Monosodium glutamate | 0.3 | $(NH_4)_4HPO_4$ | 0.3 |
| $(NH_4)_2HPO_4$ | 0.3 | $KH_2PO_4$ | 0.1 |
| $KH_2PO_4$ | 0.1 | $MgSO_4 \cdot 7H_2O$ | 0.05 |
| $MgSO_4 \cdot 7H_2O$ | 0.05 | $FeCl_2 \cdot 6H_2O$ | 0.001 |
| $FeCl_2 \cdot 6H_2O$ | 0.001 | $MnCl_2 \cdot 4H_2O$ | 0.001 |
| $MnCl_2 \cdot 4H_2O$ | 0.001 | | |

*The carbohydrate constituents of the media were sterilized separately from the other ingredients of the media.

The above-identified microorganisms were propagated in each of the media shown above by incorporating the microorganisms in 25 ml. of each medium at a pH of 6.8 and placing the inoculated media in 250 ml. shake flasks. The shake flasks were agitated at approximately 200 rpm for about 70 hours while being maintained at a temperature of 30°C. The propagations were then filtered and the cell-free broths analyzed for isoamylase activity as described above. The isoamylase activities of the broths are set forth in Table I, below.

Table I

| Microorganism | Isoamylase Activity | |
|---|---|---|
| | Medium A | Medium B |
| Flavobacterium sp. ATCC 21918 | 28.2 IU/ml | 21.3 IU/ml |
| Micrococcus sp. ATCC 21919 | 12.9 IU/ml | 0.03 IU/ml |
| Arthrobacter sp. ATCC 21920 | 6.3 IU/ml | 0.08 IU/ml |

From the above, it is apparent that the maltitol enhanced the production of isoamylase.

EXAMPLE II

This example illustrates propagating microorganisms which produce isoamylase in a medium containing pullulan as the principal carbon source and a relatively small amount of maltitol and compares the yield of isoamylase obtained with the yield of isoamylase obtained by propagating the microorganisms without the presence of maltitol.

Flavobacterium sp. ATCC 21918, Micrococcus sp. ATCC 21919 and Arthrobacter sp. ATCC 21920 were propagated under the conditions set forth in Example I in culture media having the following composition:

| Comp. of Medium A* | | Comp. of Medium B* | |
|---|---|---|---|
| Ingredient | %W/V | Ingredient | %W/V |
| Maltitol | 0.7 | Pullulan | 1.0 |
| Pullulan | 1.0 | $NaNO_3$ | 0.3 |
| $NaNO_3$ | 0.3 | $K_2HPO_4$ | 0.2 |
| $K_2HPO_4$ | 0.2 | KCl | 0.05 |
| $MgSO_4 \cdot 7H_2O$ | 0.05 | $KH_2PO_4$ | 0.05 |
| KCl | 0.05 | $MgSO_4 \cdot 7H_2O$ | 0.05 |
| $KH_2PO_4$ | 0.05 | $CaCl_2$ | 0.005 |
| $CaCl_2$ | 0.005 | $FeSO_4 \cdot 7H_2O$ | 0.001 |
| $FeSO_4 \cdot 7H_2O$ | 0.001 | | |

*The carbohydrate constituents of the media were sterilized separately from the other ingredients of the media.

After propagation, the propagation broths were filtered and the cell-free broths analyzed for isoamylase activity as described above. The isoamylase activities of the broths are set forth in Table II, below:

Table II

| Microorganism | Isoamylase Activity | |
|---|---|---|
| | Medium A | Medium B |
| Flavobacterium sp. ATCC 21918 | 0.10 IU/ml | 0.06 IU/ml |
| Micrococcus sp. ATCC 21919 | 0.54 IU/ml | 0.24 IU/ml |

Table II-continued

| Microorganism | Isoamylase Activity | |
|---|---|---|
| | Medium A | Medium B |
| Arthrobacter sp. ATCC 21920 | 4.8 IU/ml | 3.2 IU/ml |

From the above, it is seen that when pullulan was used as the principal carbon source, maltitol had a slight enhancing effect on the production of isoamylase.

The terms and expressions which have been employed are used as terms of description and not of limitation, and it is not intended by the use of such terms and expressions to exclude any equivalents of the features shown and described or portions thereof, since it is recognized that various modifications are possible within the scope of the invention claimed.

What is claimed is:

1. A process for producing isoamylase comprising propagating microorganisms which produce isoamylase in an aqueous nutrient medium having present an amount of maltitol sufficient to increase the amount of isoamylase produced over the amount of isoamylase produced by propagating the microorganisms without the presence of maltitol.

2. A process for producing isoamylase as defined in claim 1, wherein the microorganism is from the Arthrobacter genus.

3. A process for producing isoamylase as defined in claim 1, wherein the microorganism is from the Micrococcus genus.

4. A process for producing isoamylase as defined in claim 1, wherein the microorganism is from the Flavobacterium genus.

5. A process for producing isoamylase as defined in claim 2, wherein the microorganism is Arthrobacter sp. ATCC 21920.

6. A process for producing isoamylase as defined in claim 3, wherein the microorganism is Micrococcus sp. ATCC 21919.

7. A process for producing isoamylase as defined in claim 4, wherein the microorganism is Flavobacterium sp. ATCC 21918.

8. A process for producing isoamylase as defined in claim 1, wherein the amount of maltitol present is from about 0.2 to about 1.0 percent by weight based upon the volume of the propagation medium.

9. A process for producing isoamylase as defined in claim 1, wherein there is present maltose in the aqueous nutrient medium.

10. A process for producing isoamylase as defined in claim 8, wherein the amount of maltitol present is from about 0.3 to about 0.8 percent by weight based upon the volume of the propagation medium.

* * * * *